(12) United States Patent
O'Neil et al.

(10) Patent No.: US 8,433,383 B2
(45) Date of Patent: *Apr. 30, 2013

(54) STACKED ADHESIVE OPTICAL SENSOR

(75) Inventors: Michael Patrick O'Neil, Sunnyvale, CA (US); Paul Mannheimer, Danville, CA (US); Rodney Chin, Oakland, CA (US); Adnan Merchant, Fremont, CA (US); Joseph Coakley, Dublin, CA (US); Don Hannula, San Luis Obispo, CA (US)

(73) Assignee: Covidien LP, Mansfield, MA (US)

( * ) Notice: Subject to any disclaimer, the term of this patent is extended or adjusted under 35 U.S.C. 154(b) by 2033 days.

This patent is subject to a terminal disclaimer.

(21) Appl. No.: 11/482,258

(22) Filed: Jul. 7, 2006

(65) Prior Publication Data
US 2006/0276700 A1    Dec. 7, 2006

Related U.S. Application Data

(63) Continuation of application No. 10/831,706, filed on Apr. 23, 2004, now Pat. No. 7,113,815, which is a continuation of application No. 10/256,245, filed on Sep. 25, 2002, now Pat. No. 6,748, 254.

(60) Provisional application No. 60/328,924, filed on Oct. 12, 2001.

(51) Int. Cl.
*A61B 5/1455* (2006.01)
(52) U.S. Cl.
USPC ............ 600/323; 600/310; 600/322; 600/344
(58) Field of Classification Search .................. 600/310, 600/322, 323, 324, 326, 340, 344; 356/41
See application file for complete search history.

(56) References Cited

U.S. PATENT DOCUMENTS

| 3,721,813 A | 3/1973 | Condon et al. |
| 4,321,930 A | 3/1982 | Jobsis et al. |

(Continued)

FOREIGN PATENT DOCUMENTS

| DE | 3516338 | 11/1986 |
| DE | 3703458 | 8/1988 |

(Continued)

OTHER PUBLICATIONS

Faisst, Karin, et al.; "Intrapartum Reflectance Pulse Oximetry: Effects of Sensor Location and Fixation Duration on Oxygen Saturation Readings," Journal of Clinical Monitoring, vol. 13, pp. 299-302 (1997).

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

An optical sensor having a cover layer, an emitter disposed on a first side of the cover, a detector disposed on the first side of said cover, and a plurality of stacked independent adhesive layers disposed on the same first side of the cover, wherein the top most exposed adhesive layer is attached to a patient's skin. Thus, when the sensor is removed to perform a site check of the tissue location, one of the adhesive layers may also be removed and discarded, exposing a fresh adhesive surface below for reattachment to a patient's skin. The independent pieces of the adhesive layers can be serially used to extend the useful life of the product.

21 Claims, 4 Drawing Sheets

U.S. PATENT DOCUMENTS

| | | | |
|---|---|---|---|
| 4,380,240 A | 4/1983 | Jobsis et al. |
| 4,494,550 A | 1/1985 | Blazek et al. |
| 4,510,938 A | 4/1985 | Jobsis et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,089,880 A * | 2/1992 | Meyer et al. .................. 257/692 |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |

| | | |
|---|---|---|
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |

| | | |
|---|---|---|
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,879,373 A | 3/1999 | Roper et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,321,100 B1 | 11/2001 | Parker |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,381,489 B1 | 4/2002 | Ashibe |
| 6,385,471 B1 | 5/2002 | Mortz |

| | | |
|---|---|---|
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,167 B1 | 7/2002 | Blank et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |

| Patent Number | Date | Inventor |
|---|---|---|
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,583 B1 | 1/2005 | Lewandowski et al. |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,112,175 B2 | 9/2006 | Gopinathan |
| 7,113,815 B2 | 9/2006 | O'Neil et al. |
| 7,245,953 B1 | 7/2007 | Parker |
| 7,257,438 B2 | 8/2007 | Kinast |
| 7,272,425 B2 | 9/2007 | Al-Ali |
| 7,297,119 B2 | 11/2007 | Westbrook et al. |
| 7,341,559 B2 | 3/2008 | Schulz et al. |
| 7,359,741 B2 | 4/2008 | Sarussi |
| 7,435,222 B2 | 10/2008 | Gopinathan |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0103423 A1 | 8/2002 | Chin |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0069484 A1 | 4/2003 | Blank et al. |
| 2003/0073889 A1 | 4/2003 | Keilbach et al. |
| 2003/0100840 A1 | 5/2003 | Sugiura et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0054291 A1 | 3/2004 | Schulz et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0199063 A1 | 10/2004 | O'Neil et al. |
| 2004/0260161 A1 | 12/2004 | Melker et al. |
| 2005/0043599 A1 | 2/2005 | O'Mara |
| 2005/0043600 A1 | 2/2005 | Diab et al. |
| 2005/0163412 A1 | 7/2005 | Glebov et al. |
| 2006/0020179 A1 | 1/2006 | Anderson et al. |
| 2006/0064024 A1 | 3/2006 | Schnall |
| 2006/0089547 A1 | 4/2006 | Sarussi |
| 2006/0200018 A1 | 9/2006 | Al-Ali |
| 2006/0276700 A1 | 12/2006 | O'Neil et al. |
| 2007/0021659 A1 | 1/2007 | Delonzor et al. |
| 2007/0021660 A1 | 1/2007 | Delonzor et al. |
| 2007/0021662 A1 | 1/2007 | Delonzor et al. |
| 2007/0027378 A1 | 2/2007 | Delonzor et al. |
| 2007/0027379 A1 | 2/2007 | Delonzor et al. |
| 2007/0027380 A1 | 2/2007 | Delonzar |
| 2008/0009691 A1 | 1/2008 | Parker |

FOREIGN PATENT DOCUMENTS

| | | |
|---|---|---|
| DE | 19632361 | 2/1997 |
| EP | 0127947 | 5/1984 |
| EP | 0204259 | 5/1986 |
| EP | 204459 | 12/1986 |
| EP | 430340 | 6/1991 |
| EP | 0531631 | 6/1992 |
| EP | 724860 | 8/1996 |
| EP | 0724860 | 8/1996 |
| EP | 1491135 | 12/2004 |
| FR | 2685865 | 7/1993 |
| JP | 2111343 | 4/1990 |
| JP | 3245042 | 10/1991 |

| | | |
|---|---|---|
| JP | 5049625 | 3/1993 |
| JP | 6014906 | 1/1994 |
| JP | 6029504 | 4/1994 |
| JP | 6154177 | 6/1994 |
| JP | 6269430 | 9/1994 |
| JP | 6285048 | 10/1994 |
| JP | 7001273 | 1/1995 |
| JP | 7155311 | 6/1995 |
| JP | 7155313 | 6/1995 |
| JP | 7236625 | 9/1995 |
| JP | 7246191 | 9/1995 |
| JP | 10216115 | 8/1998 |
| JP | 10337282 | 12/1998 |
| JP | 20237170 | 9/2000 |
| JP | 2000237170 | 9/2000 |
| JP | 3116259 | 10/2000 |
| JP | 3116260 | 10/2000 |
| JP | 3134144 | 2/2001 |
| JP | 2002224088 | 8/2002 |
| JP | 23275192 | 9/2003 |
| JP | 2003275192 | 9/2003 |
| JP | 24089546 | 3/2004 |
| JP | 2004089546 | 3/2004 |
| JP | 2004248820 | 9/2004 |
| JP | 2004329406 | 11/2004 |
| JP | 2004329607 | 11/2004 |
| JP | 2004337605 | 12/2004 |
| JP | 2004344367 | 12/2004 |
| JP | 2004351107 | 12/2004 |
| JP | 26122693 | 5/2006 |
| WO | WO8909566 | 10/1989 |
| WO | WO09001293 | 2/1990 |
| WO | WO9001293 | 2/1990 |
| WO | WO9111137 | 8/1991 |
| WO | WO9221281 | 12/1992 |
| WO | WO9502358 | 1/1995 |
| WO | WO9616591 | 6/1996 |
| WO | WO9736536 | 10/1997 |
| WO | WO98/57577 | 12/1998 |
| WO | WO9947039 | 9/1999 |
| WO | WO0028888 | 5/2000 |
| WO | WO0059374 | 10/2000 |
| WO | WO03039326 | 5/2003 |
| WO | WO2005010567 | 2/2005 |
| WO | WO2005010568 | 2/2005 |

OTHER PUBLICATIONS

Izumi, Akio, et al.; "Accuracy and Utility of a New Reflectance Pulse Oximeter for Fetal Monitoring During Labor," Journal of Clinical Monitoring, vol. 13, pp. 103-108 (1997).

"Smaller Product, Tighter Tolerances Pose Dispensing Challenges for Medical Device Manufacturer," Adhesives Age, pp. 40-41 (Oct. 1997).

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

DeKock, Marc; "Pulse Oximetry Probe Adhesive Disks: a Potential for Infant Aspiration," Anesthesiology, vol. 89, pp. 1603-1604 (1998).

Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, vol. 20, No. 4, pp. 1906-1919.

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

König, Volker, et al.; "Reflectance Pulse Oximetry—Principles and Obstetric Application in the Zurich System," Journal of Clinical Monitoring and Computing, vol. 14, pp. 403-412 (1998).

Nogawa, Masamichi, et al.; "A Novel Hybrid Reflectance Pulse Oximater Sensor with improved Linearity and General Applicability to Various Portions of the Body," Proceedings of the 20th Annual International Conference of the IEEE Engineering in Medicine and Biology, vol. 20.

Ferrell, T.L., et al.; "Medical Telesensors," SPIE, vol. 3253, pp. 193-198 (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the $22^{nd}$ Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the $22^{nd}$ Annual EMBS International Conference, Chicago, Illinois; Jul. 23-28, 2000; pp. 2796.

Nijland, Mark J.M., et al.; "Assessment of fetal scalp oxygen saturation determination in the sheep by transmission pulse oximetry," Am. J. Obstet Gynecol., vol. 183, No. 6, pp. 1549-1553 (Dec. 2000).

Schulz, Christian Eric; "Design of a Pulse Oximetry Sensor Housing Assembly," California State University Master's Thesis, UMI Dissertation Services, UMI No. 1401306, (May 2000) 63 pages.

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.

Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," Sensor and Actuators, vol. B-76, pp. 527-530 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Lopez-Silva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Liu, Ying, et al.; "Sensor design of new type reflectance pulse oximetry," Optics in Health Care and Biomedical Optics: Diagnostics and Treatment, Proceedings of SPIE, vol. 4916, pp. 98-102 (2002).

Kyriacou, Panayiotis a., et al.; "Esophageal Pulse Oximetry Utilizing Reflectance Photoplethysmography," IEEE Transactions on Biomedical Engineering, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," Physiological Measurement, vol. 23, No. 3, pp. 533-545 (Aug. 2002).

Irie, A., et al.; "Respiration Monitors—Pulse Oximeters," Neonatal Care, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

* cited by examiner

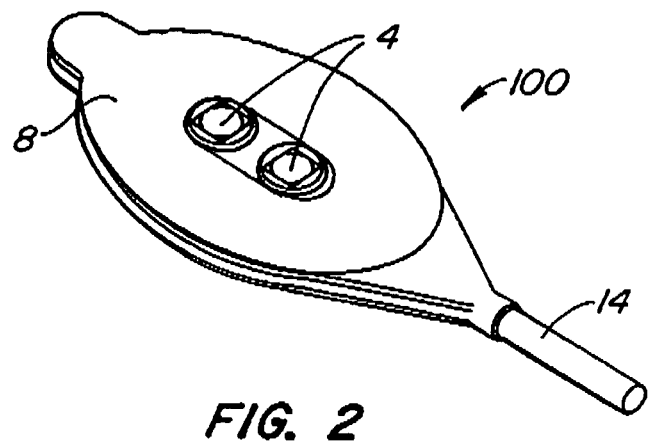
FIG. 2
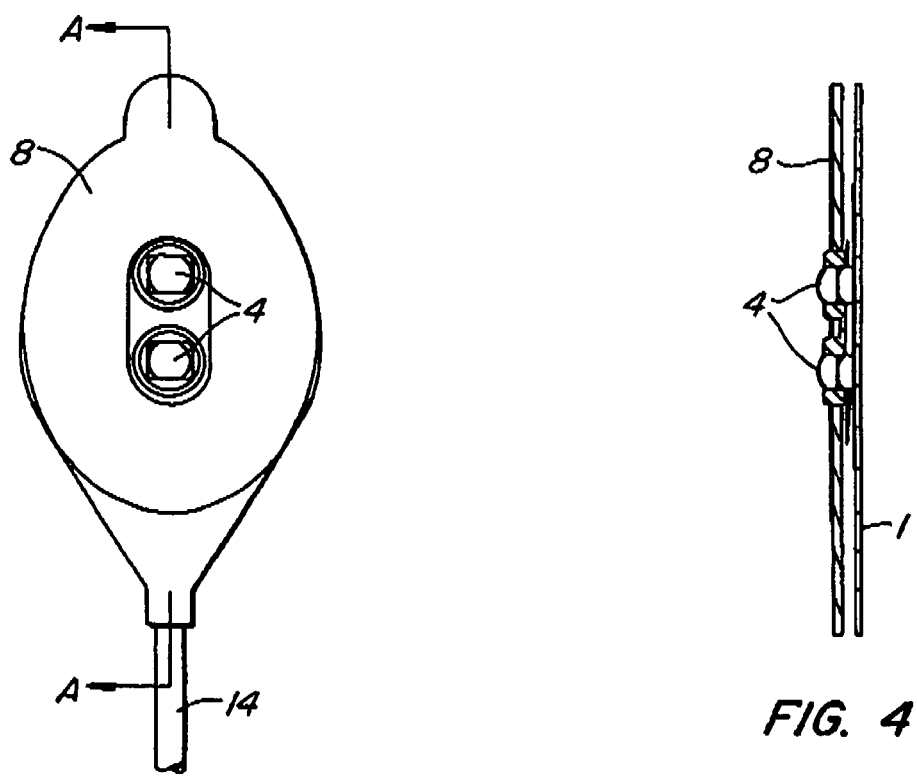
FIG. 3
FIG. 4

STACKED ADHESIVE OPTICAL SENSOR

CROSS-REFERENCE TO RELATED APPLICATION

The present application claims priority to U.S. Provisional Patent Application No. 60/328,924, filed Oct. 12, 2001, the teachings of which are incorporated herein by reference for all purposes.

This application is a continuation of U.S. patent application Ser. No. 10/831,706 filed on Apr. 23, 2004, now U.S. Pat. No. 7,113,815 which is a continuation of U.S. patent application Ser. No. 10/256,245, filed on Sep. 25, 2002, now U.S. Pat. No. 6,748,254, the full disclosures of which are incorporated herein by reference.

BACKGROUND OF THE INVENTION

The present invention relates to optical sensors, and in particular to pulse oximeter sensors.

Many types of optical sensors are used to measure physiological characteristics of a patient. Typically, an optical sensor provides emitted light which is then scattered through a portion of a patient's tissue and detected. Various characteristics of a patient can be determined from analyzing such light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Certain types of optical sensors are applied to a patient's external tissue by way of an adhesive attachment, enabled by an adhesive layer on the sensor. During the monitoring of a patient, there is a need to remove the sensor to perform a site check of the tissue location, and this removal typically damages the adhesive layer. Furthermore, adhesive type sensors are often used with disposable type sensors where the photo emitter and the detector are mounted on a backing without the benefit of a rigid optical mount to maintain the emitter and detector's separation relatively fixed, and thus the sensor is subject to motion induced artifacts that may adversely affect measurement accuracy.

There is therefore a need to improve the functionality of adhesive-type optical sensors.

BRIEF SUMMARY OF THE INVENTION

The present invention provides an optical sensor having a cover layer, an emitter disposed on a first side of the cover, a detector disposed on the first side of said cover, and a plurality of stacked independent adhesive layers disposed on the same first side of the cover, wherein the top most exposed adhesive layer is attached to a patient's skin. Thus, when the sensor is removed to perform a site check of the tissue location, one of the adhesive layers may also be removed and discarded, exposing a fresh adhesive surface below for re-attachment to a patient's skin. The independent pieces of the adhesive layers can be serially used to extend the useful life of the product.

One aspect of the present invention is directed towards using a generally annulus-shaped adhesive layer that surround the emitter and the detector and thus avoids having any adhesive present between the emitter and the detector to minimize optical shunt, which is known to adversely affect measurement accuracy.

Another aspect of the present invention is directed towards using optical lenses made from a soft or compliant material such as an optically transparent PVC material to minimize tissue necrosis.

Another aspect of the invention is directed towards the use of a semi-rigid optical mount structure to hold the emitter and the detector in place to maintain the separation between the electro-optics (emitter and detector) relatively fixed and yet allow a certain minimal amount of torque and twisting to occur as the sensor is applied. The semi-rigid optical mount, by maintaining the separation relatively fixed reduces motion induced artifacts in the detected electro-optic signals, which may adversely interfere with measurement accuracy. For a further understanding of the nature and advantages of the present invention, reference should be made to the following description in conjunction with the accompanying drawings.

BRIEF DESCRIPTION OF THE DRAWINGS

FIG. 2 is a perspective view of the sensor according to an embodiment of the present invention.

FIG. 3 is a top view of the embodiment of FIG. 2.

FIG. 4 is a sectional view "A-A" of FIG. 3.

DETAILED DESCRIPTION OF THE INVENTION

Figure 1:
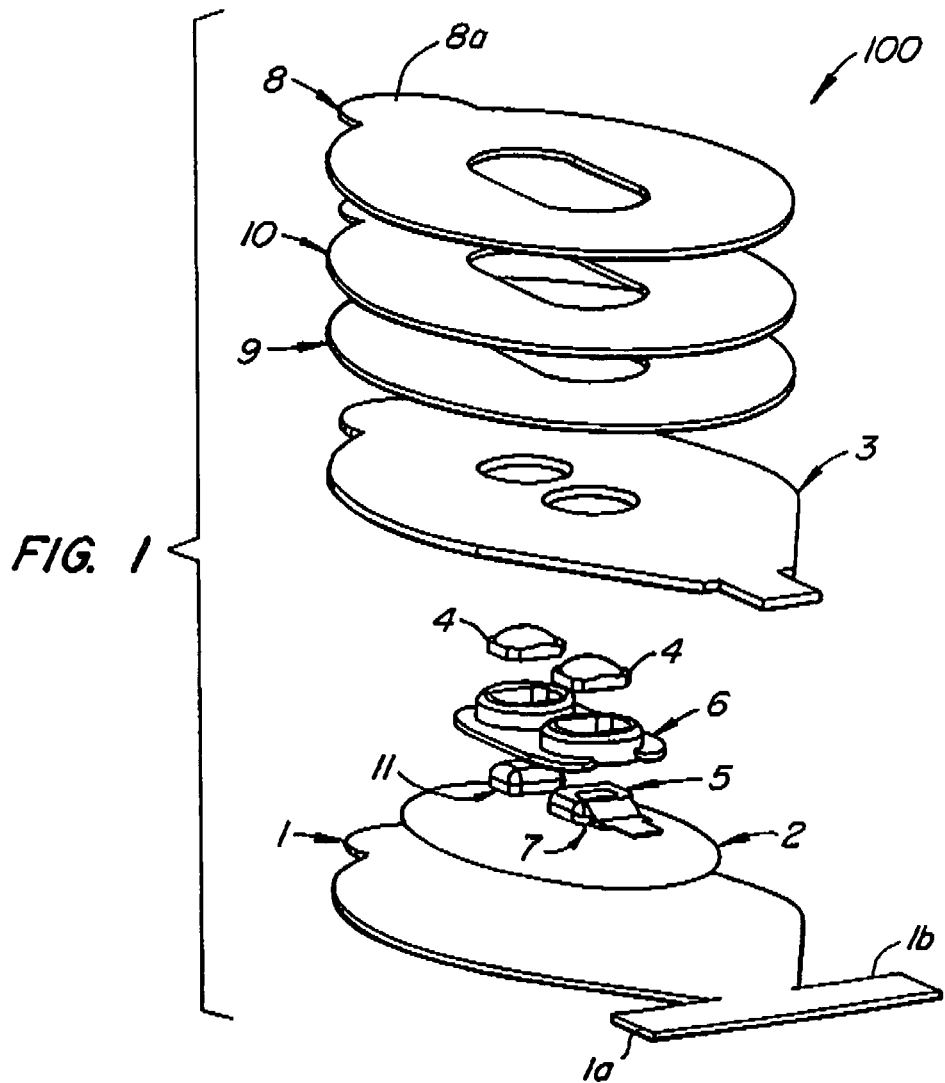
FIG. 1 is a perspective disassembled view of the sensor according to an embodiment of the present invention.

FIG. 1 is a perspective disassembled view of the sensor 100 according to an embodiment of the present invention. The sensor includes a sensor top 1 or cover layer which is exposed to the ambient environment when the sensor is attached to a patient's skin. In one embodiment, the cover layer 1 is fabricated of a common PVC foam. Alternately, the cover layer 1 is fabricated of a urethane foam material and particularly, an open cell breathable urethane foam such as, for example, the PORON™ family of urethanes commercially available from the Rogers corporation of Connecticut. A mask layer 2 preferably including a metalized plastic film is adhesively attached to the cover layer 1. In a preferred embodiment, the metalized masked layer 2 is an aluminized polypropylene film with a synthetic adhesive layer for attachment to the cover layer 1. The metalized mask layer 2 is so placed to prevent, minimize or reject secondary light from interfering with the photodetector 7. As used herein, secondary light includes all light that originates from sources other than the emitter 11, and which may have originated from sources including ambient or surgical light sources. An emitter 11 is placed above the mask layer 2. The emitter 11 is configured to direct light at predetermined wavelengths at a patient's skin. The light directed to the patient's skin is scattered through the patient's tissue and is selected to be of one or more wavelengths that are absorbed by the blood in an amount representative of the amount of blood constituent present in the body. A photo detector 7 is also placed above the mask layer 2 and adjacent to the emitter 11 to detect the amount of light that has been diffused through the patient's tissue. The amount of light that has diffused through the patient's tissue will vary in accordance with the changing amount of blood constituent in the tissue and the related light absorption.

For measuring blood oxygen level, the emitter is adapted to generate light of at least two different wavelengths, in accordance with known techniques for measuring blood oxygen saturation. The sensor, when adapted for blood oxygen saturation is useable for not only adult patients, but may also be adapted for use for neonatal and pediatric patients. Adaptations for neonatal and pediatric use may include accommodations of size and/or adhesive materials more compatible with the geometry and skin characteristics of those patients. Further, the sensor may optionally use emitters of different wavelengths and hence may use emitter and detector combinations that lead to more accurate readings at low blood oxygen saturations, which is the case for some patients. Light sources which are optimized for low oxygen saturation ranges are described in U.S. Pat. No. 5,782,237, entitled: "Pulse Oximeter and Sensor Optimized for Low Saturation," assigned to the assignee herein, the disclosure of which is hereby incorporated by reference herein in its entirety.

A Faraday shield 5 is placed in front of photodetector 7 to reduce the effect of extrinsic electrical fields that could adversely affect the electrical signal from the photodetector. A semi-rigid optical mount 6 is placed above the mask layer 2, and which surrounds and holds the emitter 11 and the detector 7 in a manner to maintain the separation between the emitter 11 and the detector 7 fixed and yet allow a certain minimal amount of flexing and twisting to occur as the sensor is applied to a patient. Without the semi-rigid optical mount in place, torque can often cause orientation changes between the emitter 11 and the detector 7 which can interfere with the accuracy of the measurements obtained by the sensor through changes in calibration and motion-induced artifact. Furthermore, the semi-rigid optical mount 6 substantially reduces the flex and the twist which may also create significant motion artifact, which is also known to adversely affect measurement accuracy. In one embodiment, the semi-rigid optical mount 6 is manufactured from a black polypropylene material. The black color of the optical mount also reduces the potential for optical shunt between the emitter and the detector, which can also cause measurement inaccuracies. Windows or lenses 4 are attached or bonded using a suitable adhesive (e.g., an ultraviolet cure adhesive process), one each to the detector and the emitter to assist in coupling the light emitted from the emitter 11 into the tissue, and collected from the tissue and directed towards the detector 7. In one embodiment, the lenses 4 are made of an optically transparent plastic material to minimize optical attenuation. In an alternate embodiment, the lenses 4 are made of a compliant material such as a transparent PVC, urethanes, or room temperature vulcanized (RTV) material, and so on. The choice of selecting a compliant material for the lenses is driven by the desire to prevent the possibility of necrosis of the skin, when the sensor is applied to the patient. Preferably, the compliant material has a hardness of less than 60 on a Shore A durometer scale. Alternately, or in addition to the lenses, the emitter and/or the detector arrangements may also include optical diffusers. The advantage of using optical diffusers is that the sensor would have less sensitivity to tissue heterogeneity, and thus provide more uniform and more accurate results.

A mask layer 3 is adhesively connected with the parts below it. The mask layer 3 has openings therein that fit over and surround the optical mount 6 placed below it (the mask layer 3). The mask layer 3 serves as a substantially flat platform for the subsequent attachment of the stack of adhesive layers. In one embodiment, the mask layer is fabricated from a cellular urethane foam such as the PORON™ family of urethane foams, and is attached to the cover layer 1 using a pressure sensitive adhesive. Lastly, a stack of adhesive layers 8, 9, and 10 are placed above the mask layer 3. The lower most adhesive layer 9 is attached to the mask layer 3 using an acrylic transfer adhesive. While in one embodiment a stack of three adhesive layers is placed above the mask layer 3, other multiple stacked adhesive layers are also within the scope of the embodiments of the present invention.

In one embodiment, the adhesive layers are in a ring shape so that no adhesive is present between the photo emitter 11 and the photo detector 7, thereby minimizing optical shunt between the photo emitter and the photo detector, which is known to lead to measurement inaccuracies. The adhesive layers or rings may be manufactured of a polyethylene film having an acrylic adhesive on one side for attachment to the patient's tissue. Alternately, the adhesive layers or rings may have an adhesive layers on both sides, in which case the adhesive layers are separated from one another by release layers (e.g. release paper). Preferably, the adhesive layers include a non-adhesive tab portion (e.g. 8*a*), arranged stacked or in a fanned-out array, to enable the clinician to easily grab and remove the used adhesive layer to expose the layer below. The tab portions may be non-adhesive colored tabs (e.g., a green, yellow, red, lavender, orange) to enable the easy removal of the adhesive rings. Additionally, another release layer (not shown) is placed above the stack of adhesive layers to cover the very first adhesive layer while it is in storage.

In certain embodiments, the adhesive rings are black to minimize reflected light, which is known to impact the accuracy of optical-based measurements. In certain embodiments, the adhesive rings are thermally stable, so that the adhesion between the rings is not compromised as a result of exposure to heat. Additionally, the adhesive rings may include a release agent, such as, for example, a low molecular weight silicone oil on the back side of the ring, in order to minimize or prevent adjacent rings from sticking to one another. Various alternate ring construction may be employed, including a continuous 0.001 inch thick polyethylene film with acrylic pressure sensitive adhesive on one side. The continuous film can be made of other materials such as polyester, polyimide or Teflon, to achieve specific strength, release and temperature stability requirements. The adhesives used on the surface of the film can be acrylic, synthetic rubber, natural rubber (e.g., latex) or other non-toxic adhesive. The ring may include a paper with a release agent on one side as the carrier film. This allows printing on each release liner, user information such as "adhesive layer #1" or can be inked black to control optical shunt.

Alternately, the adhesive rings need not be in a ring shape, but may be continuous adhesive surface, with a black strip between the emitter and detector in order to minimize optical shunt.

The pre-attached stacks of adhesive layers enables the extended use of a disposable adhesive-type sensor. A desired feature for sensors is the ability to check the sensor site periodically (e.g. once every 12 hours), and remain capable of continuous use for multiple days. In prior disposable sensors which were adhesively attached to a patient's skin, multiple cycles of repositioning the sensor was not possible due to the degradation of the adhesive and the sloughing nature of the tissue beneath the sensor attachment location. This failed reattachment would necessitate the replacement of the sensor in its entirety, which would increase the overall cost of the patient monitoring procedure. However, with the use of a stack of pre-attached adhesive rings, when the sensor is removed to perform a site check, one of the adhesive layers may also be removed exposing a fresh adhesive surface below. Thus, having several independent pieces of adhesive layers that can be serially used, extends the useful life of the product and reduces the overall costs of the patient monitoring procedure.

FIG. 2 is a perspective view of the assembled sensor 100. This figure (FIG. 2) shows the top most adhesive layer 8, and lenses 4 covering the photo emitter 11 and photo detector 7. Furthermore, FIG. 2 shows cable 14 attached to the sensor 100. Tab portions 1a and 1b (shown in FIG. 1) wrap around the cable 14 to hold the cable and the sensor in a stable manner. Cable 14 attaches to the photo emitter 11 and detector 7 via traces or wires (not shown).

FIG. 3 is a top view of the embodiment of FIG. 2. FIG. 3 also shows the top most adhesive layer 8, and lenses 4 covering the photo emitter 11 and photo detector 7. Furthermore, FIG. 2 shows cable 14 attached to the sensor 100. FIG. 4 shows sectional view "A-A" of FIG. 3. FIG. 4 shows the cover layer 1, the top most adhesive layer 8 and lenses 4 which are placed above the photo emitter 11 and photo detector 7. As can be seen from FIG. 4, the sensor 100 is substantially flat, while the lenses 4 protrude outward from a plane of the sensor. Thus, when attached, the lenses push on the patient's tissue location (e.g. forehead) to enhance light coupling and the depth of optical penetration by pressing mildly into the skin. Since the lenses protrude outward from the sensor plane, the adjacent adhesive layers necessarily lie in a plane which is offset or away from the patient's tissue location, thus "pulling" the lenses into the skin during use. This assures good optical contact between sensor and tissue, and reduces the potential contribution of light shunting.

Figure 5:
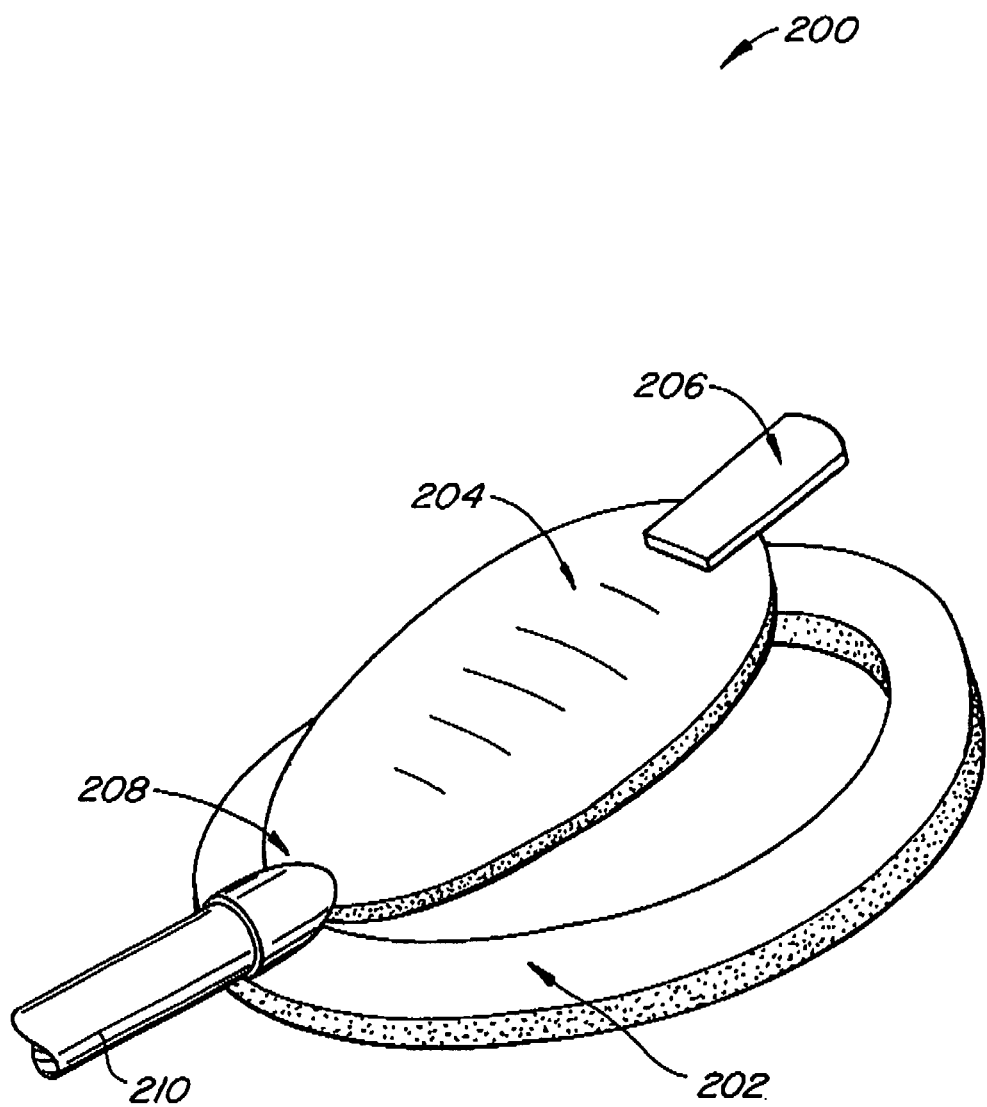
FIG. 5 is a perspective view of an alternate embodiment of the sensor of the present invention having a hinged lid.

FIG. 5 is a perspective view of an alternate embodiment of the sensor 200 of the present invention having a hinged lid. The sensor 200 includes a ring-shaped layer 202 having an adhesive side, which is configured to be attached to a patient during monitoring. The sensor 200 also includes a hinged lid 204 which holds the necessary electro-optics including a photo emitter and a photo detector (not shown) as described above. The hinged lid 204 is coupled to the ring-shaped adhesive layer 202 by a hinged connection 208 that enables the lifting and the checking of the sensor site without the need to remove the sensor from the patient. Cable 210 provides the leads or wires connected with the photo detector and photo emitter for the proper operation of the sensor. A clasp 206 secures the hinged lid 204 in a position effective for patient monitoring. The clasp 206 is also used by a clinician to lift the hinged lid 204 for checking the sensor site. In one embodiment, the clasp 206 adhesively engages the ring-shaped layer 202. In an alternate embodiment, the clasp 206 engages the ring-shaped layer via a mechanical clasp-type connection. The ring-shaped layer 202 may also incorporate a stacked adhesive arrangement as described above to enable the repeated removal and re-attachment of the sensor to the patient.

Figure 6:
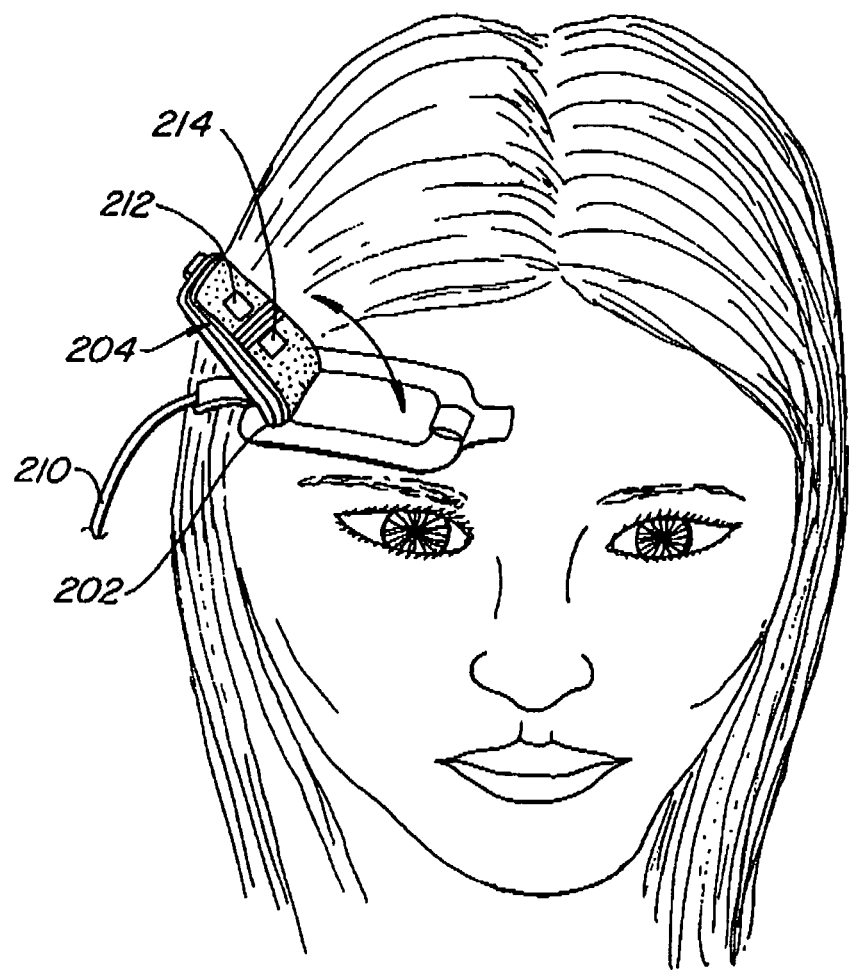
FIG. 6 is a diagram showing the sensor of FIG. 5 positioned on a patient during a site check.

FIG. 6 is a diagram showing the sensor of FIG. 5 positioned on a patient during a site check. As can be seen from this figure (FIG. 6), the ring-shaped layer 202 is adhesively attached to a patient, while the hinged lid 204 containing the photo emitter 212 and photo detector 214 is lifted from the patient's forehead to enable the checking of the tissue location underneath the sensor site. Cable 210 provides the leads or wires connected with the photo detector and photo emitter for the proper operation of the sensor.

The multiple stacked adhesive layer embodiments and the hinged lid embodiments of the present invention may be also be used to improve the operation of any disposable sensor and particularly disposable oximeter sensors. These disposable sensors include sensors based on the reflectance of light from tissue to the detector (as described above with the emitter and the detector placed on the same side of the tissue) as well as transmissive type sensors, where the emitter and the detector are placed on opposite sides of a tissue site being probed. Examples of sensors that can incorporate the multiple stacked adhesive layer embodiments or the hinged-lid embodiments include the adhesive, and reusable sensors for use at various tissue locations, including the finger tip, foot, nose, and forehead locations such as the D-20, D-25, N-25, I-20, R-15, as well as the A, N, I, and P series of sensors manufactured by the assignee herein.

Furthermore, the multiple stacked adhesive layer embodiments and the hinged lid embodiments of the present invention are not only useable for adult patients, but are also useable with patients on whom it is sometimes preferable to use a soft gel adhesive to minimize the occurrence of tearing of the skin. Such patients include geriatric, pediatric or neonatal patients. The inclusion of a soft gel in an optical sensor is described in U.S. Pat. No. 5,830,136, entitled: "Gel Pad Optical Sensor," assigned to the assignee herein, the disclosure of which is hereby incorporated herein in its entirety. An alternate embodiment of a soft gel adhesive includes only a single adhesive layer (not stacked), since some gel materials can be cleaned with water or other liquid agents to refresh the adhesive properties. As such, the use of multiple layers of gel adhesive may not be required for limited but multiple sensor placements on an individual patient.

As will be understood by those skilled in the art, the present invention may be embodied in other specific forms without departing from the essential characteristics thereof. For example, the disposable sensor may be a forehead or a nasal sensor, the sensor may be configured for use on an adult, pediatric or neonatal patient, the sensor may use several possible arrangements of adhesive layers arranged in an stacked manner, or the sensor may use suitable materials other than those described above. These other embodiments are intended to be included within the scope of the present invention, which is set forth in the following claims.

What is claimed is:

1. A sensor comprising:
   a reflectance type sensor body;
   an emitter and a detector coupled to the reflectance type sensor body, wherein the emitter and the detector are positioned at a substantially fixed distance relative to one another when the sensor is applied to a patient; and
   a semi-rigid optical mount coupled to the reflectance type sensor body, wherein the semi-rigid optical mount is configured to surround the emitter and the detector in order to hold the emitter and the detector at the substantially fixed distance, wherein the semi-rigid optical mount comprises a first aperture and a second aperture sized to hold the emitter and the detector, respectively.

2. The sensor of claim 1, wherein the sensor comprises a pulse oximetry sensor.

3. The sensor of claim 1, wherein the semi-rigid optical mount is coupled to the non-rigid portion of the sensor body.

4. The sensor of claim 1, wherein the semi-rigid optical mount comprises a polypropylene material.

5. The sensor if claim 1, wherein the semi-rigid optical mount is black.

6. The sensor of claim 1, wherein the emitter and the detector are coupled to a patient contact side of the sensor body, and wherein the sensor comprises a plurality of stacked independent adhesive layers disposed on the patient contact side of the sensor body, the plurality of stacked independent adhesive layers being configured to adhere to a tissue location on a patient.

7. The sensor of claim 1, comprising a sensor base having an opening therein, and wherein the sensor body is configured to be disposed in the sensor base, and wherein one end of the sensor body is pivotally connected to the sensor base.

8. The sensor of claim 7, comprising a clasp connected with another end of the sensor body, and wherein the clasp is configured to engage the sensor base.

9. The sensor of claim 7, comprising an adhesive layer disposed on a patient contact side of the sensor base, the adhesive layer configured to adhere to a tissue location on a patient.

10. The sensor of claim 1, wherein the emitter and detector protrude beyond a patient contact side of the sensor body.

11. A sensor comprising:
a non-rigid reflectance type sensor body;
an emitter and a detector, wherein the emitter and the detector are sized to be disposed within a first aperture and a second aperture of a semi-rigid optical mount; and
the semi-rigid optical mount coupled to the non-rigid reflectance type sensor body, wherein the semi-rigid optical mount surrounds the emitter and the detector in order to hold the emitter and the detector at a substantially fixed distance relative to one another when the sensor is applied to a patient and wherein the semi-rigid optical mount is configured to maintain the emitter and detector in a fixed orientation that resists motion-induced flexing.

12. The sensor of claim 11, wherein the sensor comprises a pulse oximetry sensor.

13. The sensor of claim 11, wherein the semi-rigid optical mount comprises a polypropylene material.

14. The sensor of claim 11, wherein the semi-rigid optical mount is black.

15. The sensor of claim 11, wherein the emitter and the detector are coupled to a patient contact side of the non-rigid sensor body, and wherein the sensor comprises a plurality of stacked independent adhesive layers disposed on the patient contact side of the non-rigid sensor body, the plurality of stacked independent adhesive layers being configured to adhere to a tissue location on a patient.

16. The sensor of claim 11, comprising a sensor base having an opening therein, and wherein the non-rigid sensor body is configured to be disposed in the sensor base, and wherein one end of the non-rigid sensor body is pivotally connected to the sensor base.

17. The sensor of claim 16, comprising a clasp connected with another end of the non-rigid sensor body, and wherein the clasp is configured to engage the sensor base.

18. The sensor of claim 16, comprising an adhesive layer disposed on a patient contact side of the sensor base, the adhesive layer configured to adhere to a tissue location on a patient.

19. The sensor of claim 11, wherein the emitter and the detector protrude beyond a patient contact side of the non-rigid sensor body.

20. A method comprising:
applying a reflectance type sensor to a patient, wherein the reflectance type sensor comprises,
a non-rigid sensor body,
an optical emitter and a photodetector disposed a fixed distance apart such that the patient's movements do not alter the fixed distance, and;
a semi-rigid optical mount coupled to the non-rigid sensor body, wherein the semi-rigid optical mount surrounds the optical emitter and the photodetector in order to hold the optical emitter and the photodetector at the fixed distance, and wherein the optical emitter and the photodetector are sized to be disposed within a first aperture and a second aperture of the semi-rigid optical mount.

21. A method of manufacturing a pulse oximetry sensor, comprising:
providing a flexible reflectance type sensor body to which an emitter and a detector are coupled, wherein the reflectance type sensor body is a non-rigid sensor body configured to hold the emitter and the detector at a substantially fixed distance relative to one another, and
providing a semi-rigid optical mount coupled to the non-rigid sensor body, wherein the semi-rigid optical mount surrounds the emitter and the detector in order to hold the emitter and the detector at the substantially fixed distance, and wherein the emitter and the detector are sized to be disposed within a first aperture and a second aperture of the semi-rigid optical mount.

* * * * *